(12) United States Patent
Samejima et al.

(10) Patent No.: US 11,324,951 B2
(45) Date of Patent: May 10, 2022

(54) ELECTRICAL TREATMENT DEVICE, CONTROL METHOD, AND TREATMENT SYSTEM

(71) Applicant: OMRON HEALTHCARE Co., Ltd., Kyoto (JP)

(72) Inventors: Mitsuru Samejima, Kyoto (JP); Yui Watanabe, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 156 days.

(21) Appl. No.: 16/736,193

(22) Filed: Jan. 7, 2020

(65) Prior Publication Data

US 2020/0139123 A1 May 7, 2020

Related U.S. Application Data

(63) Continuation of application No. PCT/JP2018/022371, filed on Jun. 12, 2018.

(30) Foreign Application Priority Data

Jul. 27, 2017 (JP) .............................. JP2017-145460

(51) Int. Cl.
 *A61N 1/36* (2006.01)
(52) U.S. Cl.
 CPC ..... *A61N 1/36034* (2017.08); *A61N 1/36031* (2017.08)
(58) Field of Classification Search
 CPC ............ A61N 1/36034; A61N 1/36031; A61N 1/0492; A61N 1/36
 (Continued)

(56) References Cited

U.S. PATENT DOCUMENTS

2010/0076516 A1\* 3/2010 Padiy .................. A61N 1/3708
 607/29
2010/0161001 A1\* 6/2010 DiUbaldi ........... A61N 1/36031
 607/59
(Continued)

FOREIGN PATENT DOCUMENTS

DE  11 2017 006 724 T5  10/2019
JP      2009125510 A     6/2009
(Continued)

OTHER PUBLICATIONS

International Search Report of the International Searching Authority for PCT/JP2018/022371 dated Sep. 11, 2018.
(Continued)

*Primary Examiner* — Amanda K Hulbert
*Assistant Examiner* — Philip C Edwards
(74) *Attorney, Agent, or Firm* — Birch, Stewart, Kolasch & Birch, LLP

(57) ABSTRACT

An electrical treatment device (200) includes a remaining power detection unit (302) that detects a remaining battery power of the electrical treatment device (200); a treatment content setting unit (306) that sets a treatment content; an impedance measurement unit (304) that measures a bioelectrical impedance of a site on a body of a user by using electrodes that come into contact with the site; a treatment execution unit (312) that performs treatment of the site by controlling a voltage waveform applied to the electrodes; and a determination unit (310) that determines whether treatment in accordance with the treatment content can be executed up until a treatment time elapses on the basis of a current remaining battery power and a power consumption calculated from the bioelectrical impedance and the voltage waveform. When treatment in accordance with the treatment content cannot be executed up until the treatment time elapses, the treatment execution unit (312) modifies a volt- (Continued)

age waveform corresponding to the treatment content currently set so that treatment can be executed up until the treatment time elapses, and outputs the modified voltage waveform.

10 Claims, 11 Drawing Sheets

(58) Field of Classification Search
USPC .......................................................... 607/59
See application file for complete search history.

(56) References Cited

U.S. PATENT DOCUMENTS

| 2017/0197077 | A1* | 7/2017 | Harpak | A61B 5/6843 |
| 2018/0133471 | A1* | 5/2018 | Lee | A61N 1/02 |
| 2019/0321622 | A1 | 10/2019 | Samejima et al. | |

FOREIGN PATENT DOCUMENTS

| JP | 2010504770 A | 2/2010 |
| JP | 2012239513 A | 12/2012 |
| JP | 2016067574 A | 5/2016 |

OTHER PUBLICATIONS

Translation of the International Search Report of the International Searching Authority for PCT/JP2018/022371 dated Sep. 11, 2018.
German Office Action for German Application No. 11 2018 003 091.1, dated Oct. 29, 2021, with English translation.

* cited by examiner

ELECTRICAL TREATMENT DEVICE, CONTROL METHOD, AND TREATMENT SYSTEM

CROSS-REFERENCE TO RELATED APPLICATIONS

This is a continuation of International Application PCT/JP2018/022371, with an international filing date of Jun. 12, 2018, filed by applicant, the disclosure of which is hereby incorporated by reference in its entirety.

TECHNICAL FIELD

The present disclosure relates to an electrical treatment device, a control method, and a treatment system.

BACKGROUND ART

A known electrical treatment device provides electrical stimulation by outputting a low-frequency pulse to muscles within the body via a plurality of pads attached to the surface regions of the body, such as the abdomen and the back.

For example, JP 2009-125510 A (Patent Document 1) describes a health promotion device which is a low-frequency treatment device with a swelling measurement function. The health promotion device includes a swelling measurement unit that measures swelling of a part of the body of the user by measuring impedance when a current flows through two measurement current electrodes on either side of the part of the body, and a low-frequency treatment unit that includes a low-frequency electrode through which a low frequency current flows to cause muscle contraction.

CITATION LIST

Patent Literature

Patent Document 1: JP 2009-125510 A

SUMMARY OF INVENTION

Technical Problem

Known low-frequency treatment devices include portable devices that use a battery as a power source. When treatment is performed using such a low-frequency treatment device, the treatment may be interrupted by the device running too low on remaining battery power during treatment. The low-frequency treatment device according to Patent Document 1 does not teach nor suggest any technology for solving the above-described problem.

An object of an embodiment of the present disclosure is to provide an electrical treatment device, a control method, and a treatment system in which executing treatment depending on a remaining battery power can prevent treatment from being interrupted.

Solution to Problem

An electrical treatment device according to an embodiment includes
a remaining power detection unit configured to detect a remaining battery power of the electrical treatment device;
a treatment content setting unit configured to set a treatment content specified by a user;
an impedance measurement unit configured to measure a bioelectrical impedance of a site on a body of the user by using electrodes that come into contact with the site;
a treatment execution unit configured to perform treatment of the site in accordance with the treatment content by controlling a voltage waveform applied to the electrodes; and
a determination unit configured to determine whether treatment in accordance with the treatment content can be executed up until a treatment time elapses on the basis of a current remaining battery power and a power consumption calculated from the bioelectrical impedance and the voltage waveform. When treatment in accordance with the treatment content cannot be executed up until the treatment time elapses, the treatment execution unit modifies a voltage waveform corresponding to the treatment content currently set so that treatment can be executed up until the treatment time elapses, and outputs the modified voltage waveform.

Preferably, the treatment execution unit modifies the voltage waveform by reducing an amplitude of the voltage waveform and increasing a pulse width of the voltage waveform.

Preferably, the treatment execution unit modifies the voltage waveform by reducing a frequency of the voltage waveform.

Preferably, when treatment in accordance with the treatment content cannot be executed up until the treatment time elapses, the treatment execution unit outputs voltage waveforms corresponding to a plurality of patterns for a predetermined amount of time. The electrical treatment device further includes an input unit configured to receive an input of a desired pattern from the user, the desired pattern being one of the plurality of patterns. Also, the treatment execution unit modifies a voltage waveform corresponding to the treatment content currently set to a voltage waveform corresponding to the pattern received.

Preferably, when a treatment content is changed by the user during treatment of the site by the treatment execution unit, the determination unit further determines whether treatment in accordance with a post-modification treatment content can be executed up until the treatment time elapses. In a case where treatment in accordance with the post-modification treatment content can be executed up until the treatment time elapses, the treatment execution unit outputs a voltage waveform corresponding to the post-modification treatment content.

Preferably, the electrical treatment device is a low-frequency treatment device.

A control method of an electrical treatment device according to another embodiment includes
detecting a remaining battery power of the electrical treatment device;
setting a treatment content specified by a user;
measuring a bioelectrical impedance of a site on a body of the user by using electrodes that come into contact with the site;
executing treatment of the site in accordance with the treatment content by controlling a voltage waveform applied to the electrodes; and
determining whether treatment in accordance with the treatment content can be executed up until a treatment time elapses on the basis of a current remaining battery power and a power consumption calculated from the bioelectrical impedance and the voltage waveform. When treatment in accordance with the treatment content cannot be executed up until the treatment time elapses, in the executing, a voltage waveform corresponding to the treatment content currently set is modified so that treatment can be executed up until the treatment time elapses, and the modified voltage waveform is output.

A treatment system according to yet another embodiment includes a terminal device; and an electrical treatment device configured to wirelessly communicate with the terminal device. The electrical treatment device includes a remaining power detection unit configured to detect a remaining battery power of the electrical treatment device;

a treatment content setting unit configured to set a treatment content specified by a user;

an impedance measurement unit configured to measure a bioelectrical impedance of a site on a body of the user by using electrodes that come into contact with the site;

a treatment execution unit configured to perform treatment of the site in accordance with the treatment content by controlling a voltage waveform applied to the electrodes; and a determination unit configured to determine whether treatment in accordance with the treatment content can be executed up until a treatment time elapses on the basis of a current remaining battery power and a power consumption calculated from the bioelectrical impedance and the voltage waveform. When treatment in accordance with the treatment content cannot be executed up until the treatment time elapses, the treatment execution unit modifies a voltage waveform corresponding to the treatment content currently set so that treatment can be executed up until the treatment time elapses, and outputs the modified voltage waveform.

Advantageous Effects of Invention

According to the present disclosure, executing treatment depending on a remaining battery power can prevent treatment from being interrupted.

DESCRIPTION OF EMBODIMENTS

Embodiments of the present invention will be described below with reference to the drawings. In the following description, like components are given like numerals. Names and functions thereof are also the same. Thus, the detailed description of such components is not repeated.

First Embodiment

Appearance

Figure 1:
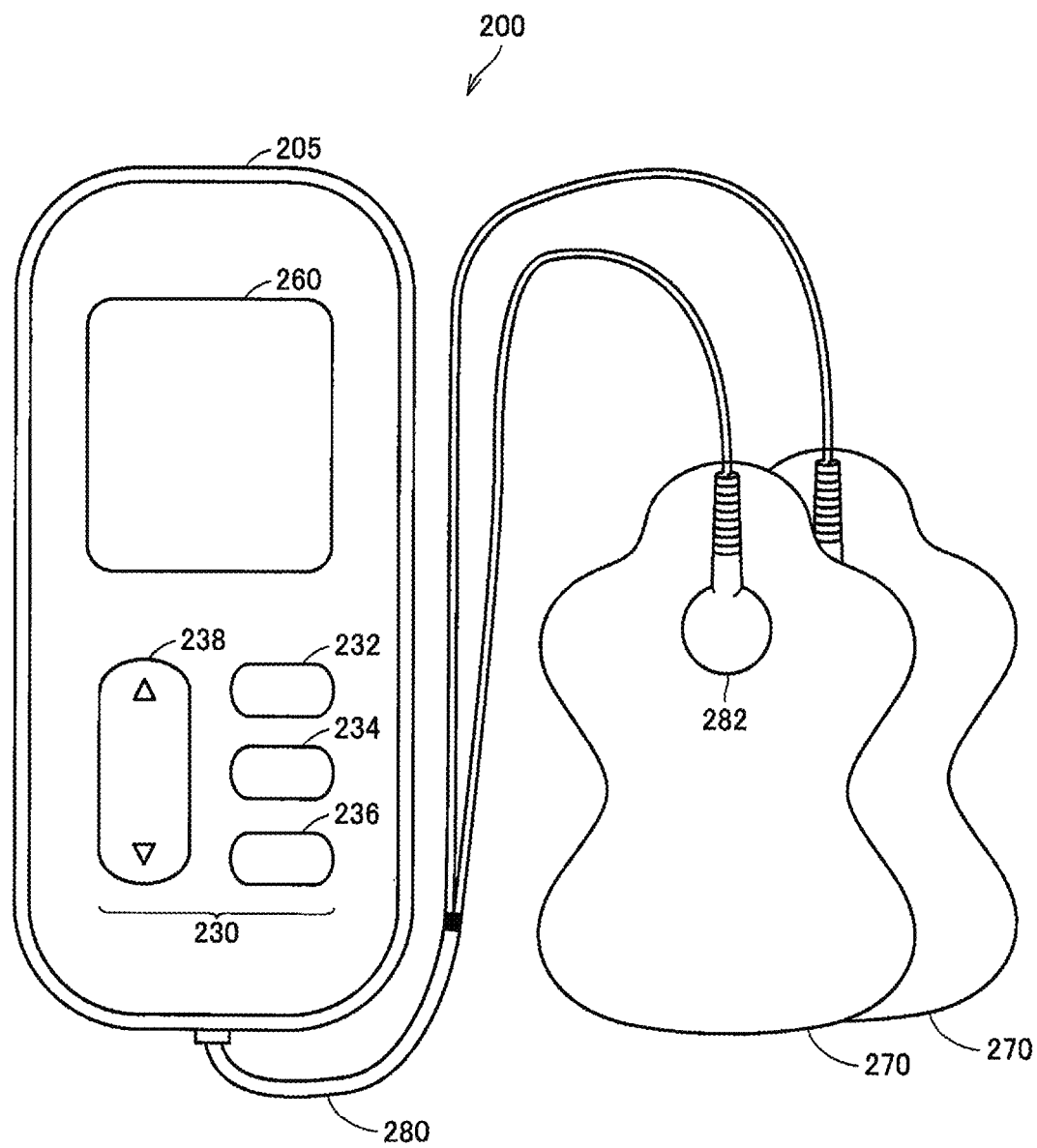
FIG. 1 is a diagram illustrating an example of the appearance of an electrical treatment device according to a first embodiment.

FIG. 1 is a diagram illustrating an example of the appearance of an electrical treatment device according to the first embodiment.

Referring to FIG. 1, an electrical treatment device 200 according to the first embodiment includes, as a main configuration, a main body portion 205 of the treatment device, a pair of pads 270 that attach to a treatment site, and a cord 280 for electrically connecting the main body portion 205 and the pads 270. The electrical treatment device 200 is a wired type, low-frequency treatment device that provides treatment such as easing user shoulder stiffness by supplying a low-frequency pulse. For example, the frequency of the low-frequency pulse current is from 1 Hz to 1200 Hz. However, the electrical treatment device 20 may be configured to use a pulse current of other frequency bands.

The pads 270 have a sheet-like shape and are configured to attach to the user's body. The surface on one side of the pad 270 (the surface that does not come into contact with the body) is provided with a plug that corresponds to an electrode (not illustrated) formed on the surface on the other side (the surface that comes into contact with the body). The electrode is formed from a conductive gel-like material, for example. To connect the main body portion 205 and the pad 270, a plug 282 of the cord 280 is connected to the plug on the pad 270 and the cord 280 is inserted into the jack on the main body portion 205. Note that when the polarity of the electrode formed on one of the pads 270 is positive, the polarity of the electrode formed on the other pad 270 is negative.

The main body portion 205 includes an operation interface 230 including various buttons; and a display 260. The operation interface 230 includes a power button 232 for switching the power source on and off, a mode selection button 234 for selecting a treatment mode, a treatment start button 236, and an adjustment button 238 for adjusting the intensity of the electrical stimulation (also referred to below as "electrical stimulation intensity"). Note that the operation interface 230 is not limited to the configuration described above and may have any configuration that allows the user to perform the various operations described below. The operation interface 230 may include other buttons, a dial, and a switch.

The electrical stimulation intensity, the remaining treatment time, the treatment mode, the attachment state of the pads 270, and the like are displayed on the display 260. Various messages are also displayed on the display 260.

Hardware Configuration

Figure 2:
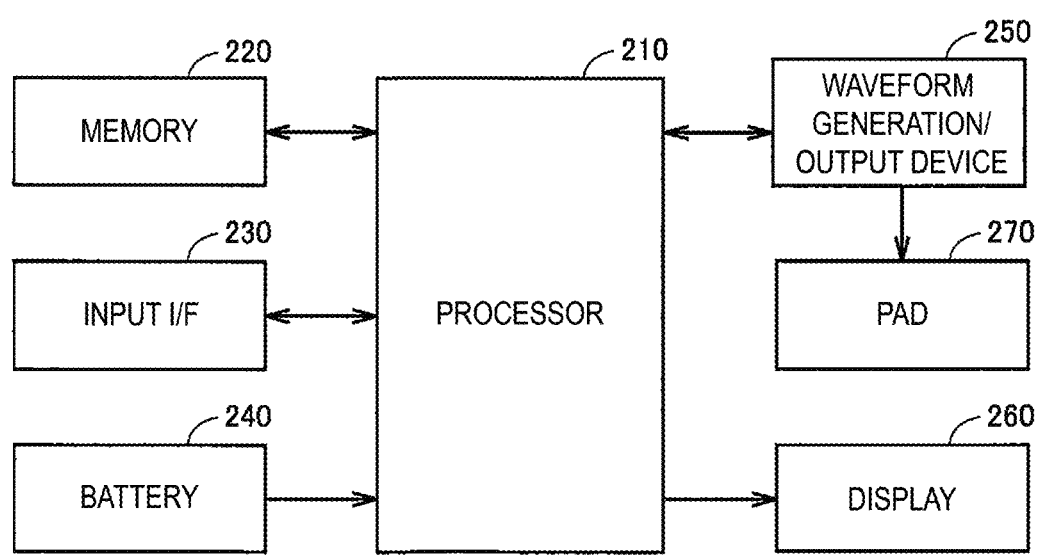
FIG. 2 is a block diagram illustrating an example of a hardware configuration of the electrical treatment device according to the first embodiment.

FIG. 2 is a block diagram illustrating an example of a hardware configuration of the electrical treatment device 200 according to the first embodiment. Referring to FIG. 2, the electrical treatment device 200 includes, as main components, a processor 210, a memory 220, an operation interface 230, a battery 240, a waveform generation/output device 250, and the display 260.

The processor 210 typically may be an arithmetic processing unit such as a central processing unit (CPU) or a multi processing unit (MPU). The processor 210 functions as a control unit that controls the operation of components of the electrical treatment device 200 by reading out and executing a program stored in the memory 220. By executing the program, the processor 210 executes processing (steps) of the electrical treatment device 200 described later.

The memory 220 is realized by random access memory (RAM), read-only memory (ROM), flash memory, and the like. The memory 220 stores programs executed by the processor 210, data used by the processor 210, and the like.

The operation interface 230 receives an operation input to the electrical treatment device 200 and includes various buttons such as those described above. When the user operates the buttons, a signal corresponding to the operation is input to the processor 210.

The battery 240 supplies power to the components of the electrical treatment device 200. The battery 240 is constituted of, for example, a rechargeable battery, such as a lithium ion battery or a nickel hydrogen battery, or an alkaline battery. The battery 240 generates a drive voltage that stabilizes the battery voltage and supplies it to each component.

The waveform generation/output device 250 outputs a current (also referred to below as a "treatment current") to a treatment site on the user's body via the pads 270. The waveform generation/output device 250 includes a booster circuit, a voltage adjustment circuit, an output circuit, a current detection circuit, and the like.

The booster circuit boosts the power supply voltage to a predetermined voltage. The voltage adjustment circuit adjusts the voltage boosted by the booster circuit to a voltage corresponding to the electrical stimulation intensity set by the user. Specifically, the electrical stimulation of the electrical treatment device 200 can be adjusted to a predetermined number of levels (for example, ten levels) via the adjustment button 238. The processor 210 receives a setting input of the electrical stimulation intensity via the adjustment button 238 and instructs the waveform generation/output device 250 (voltage adjustment circuit) to adjust to a voltage corresponding to the received electrical stimulation intensity.

The output circuit generates a voltage waveform (pulse voltage waveform) corresponding to the treatment mode on the basis of the voltage adjusted by the voltage adjustment circuit and outputs the voltage waveform to the (electrodes of) pads 270 via the cord 280. Specifically, when the user performs an operation, such as switching the treatment mode or changing the electrical stimulation intensity, via the operation interface 230, a control signal corresponding to the operation content is input to the output circuit from the processor 210. The output circuit outputs a voltage waveform in accordance with the control signal.

In this example, the electrical treatment device 200 is provided with a plurality of treatment modes in advance. The treatment modes include, for example, "massage", "tap", and "press".

The output circuit can generate an electrical stimulation corresponding to various modes including "massage", "tap", and "press" by the pulse voltage waveform (including pulse width, pulse interval, and output polarity) or the like being changed. Also, by changing the amplitude of the pulse, the electrical stimulation intensity can be adjusted. Specifically, a known voltage waveform can be used.

Figure 3:
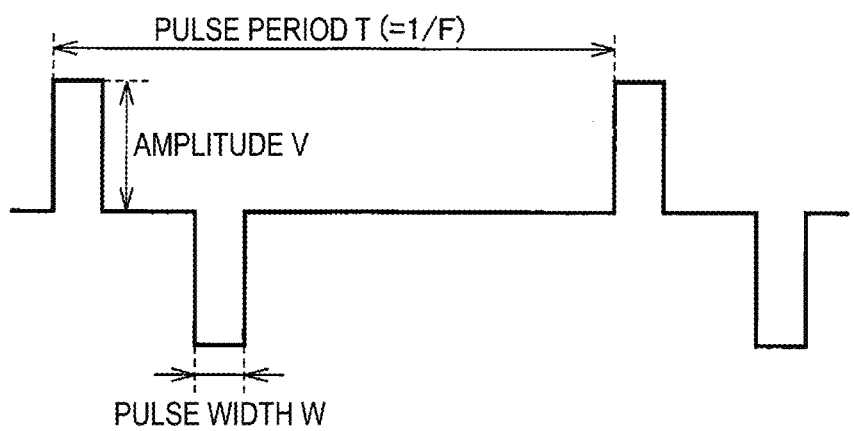
FIG. 3 is a diagram for describing parameters of a pulse voltage waveform.

FIG. 3 is a diagram for describing parameters of the pulse voltage waveform. Referring to FIG. 3, the parameters of the pulse voltage waveform include an amplitude (voltage) V, a pulse width W, and a pulse period T (i.e., pulse frequency F=1/T). The processor 210 can change the treatment for the user by changing at least one parameter of the three parameters.

Referring again to FIG. 2, the current detection circuit detects a value for the current flowing between the pair of pads 270 and inputs a signal indicating the detected value to the processor 210. Specifically, the processor 210 instructs the waveform generation/output device 250 (voltage adjustment circuit) to apply a minute voltage between the pair of pads 270 so that a minute current for bioelectrical impedance measurement flows to a treatment site on the user's body. The voltage adjustment circuit applies a minute voltage in accordance with an instruction from the processor 210. The processor 210 calculates (measures) a bioelectrical impedance R of the treatment site on the basis of the value of the minute voltage and the value of the current flowing between the pair of pads 270 through the treatment site input from the current detection circuit. Note that the minute current is a current low enough to not stimulate the user's body (the current value being 2 mA or less for example).

Also, from the current value input from the current detection circuit, the processor 210 can detect whether the pads 270 are attached (stuck) to the user or whether the pads 270 are not attached to (fallen off from) the user.

Specifically, when the current value is a predetermined value or greater, the processor 210 determines that the electrodes are in contact (i.e., the pair of pads 270 are attached to the user). When the current value is less than a predetermined value, the processor 210 determines that at least one of the electrodes is not in contact (at least one of the pair of pads 270 is not attached to the user). This utilizes the principle that, in the case where at least one of the pair of pads 270 is not properly attached to the user, a current loop, whereby the current output from one of the pads 270 returns to the other of the pads 270 through the human body, is not established, and thus a current of a predetermined value or greater does not flow.

The display 260 is constituted of, for example, a liquid crystal display (LCD) and displays various information in accordance with an instruction from the processor 210.

Modifying the Voltage Waveform

After the user attaches the pair of pads 270 to the treatment site on the body and a start treatment instruction is provided to the main body portion 205 via operation of the operation interface 230, treatment for the set treatment time (for example, 30 minutes) is started. The user typically desires that the treatment is performed fully without interruption. However, depending on the treatment content (for example, treatment mode and electrical stimulation intensity) specified by the user and the current level of remaining battery power (i.e., remaining power of the battery), treatment in accordance with the treatment content may not be able to be fully executed.

In the electrical treatment device 200 according to the first embodiment, modifying the pulse voltage waveform corresponding to the treatment content currently set and reducing power consumption prevents interruption in the middle of treatment.

The relationship between voltage waveform and power consumption will now be described. As described with reference to FIG. 3, the parameters of the pulse voltage waveform include the amplitude V, the pulse width W, and the pulse period T (i.e., pulse frequency F=1/T). Using these parameters and the bioelectrical impedance R, a power consumption P, which represents the energy used per unit time (for example, per second), may be expressed by Formula (1) below.

$$P=(V^2/R) \times W \times F \quad (1)$$

Since the remaining battery power decreases faster as the power consumption P increases, the pulse voltage waveform needs to be modified so that the power consumption P decreases in order not to interrupt the treatment. Specifically, by multiplying the power consumption P by the treatment time, a total power consumption Ph for the treatment time is calculated. The pulse voltage waveform needs to be modified so that at least the total power consumption Ph is less than the current remaining battery power.

On the other hand, the levels of electrical stimulation provided to the user before and after a modification to the pulse voltage waveform are desirably maintained as equal as possible. Thus, in the present embodiment, modified patterns such as those illustrated in FIGS. 4 and 5 are used, for example.

Figure 4:
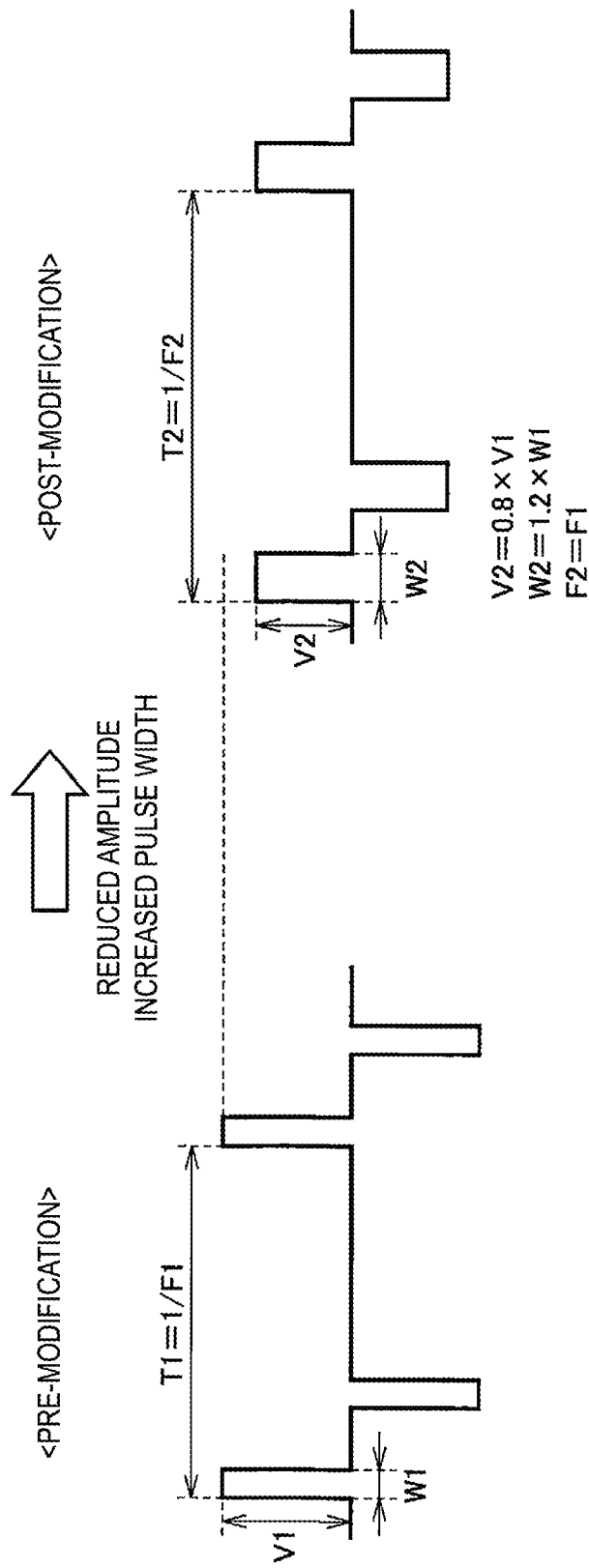
FIG. 4 is a diagram illustrating an example of a modified pattern of the pulse voltage waveform.

FIG. 4 is a diagram illustrating an example of a modified pattern of the pulse voltage waveform. Referring to FIG. 4, the parameters of the pre-modification pulse voltage waveform are an amplitude V1, a pulse width W1, and a pulse frequency F1 (=1/T1). The parameters of the post-modification pulse voltage waveform are an amplitude V2 (=0.8× V1), a pulse width W2 (=1.2×W1), and a pulse frequency F2 (=F1). That is, compared to the pre-modification pulse voltage waveform, the post-modification pulse voltage waveform has a 20% reduced amplitude and a 20% increased pulse width.

For example, substituting V1=50 (V), W1=50 (μB), F1=100 (Hz), and R=1 (kΩ) into Formula (1), a pre-modification power consumption P1 is 12.5 (mW). Substituting V2=40 (V), W2=60 (μs), and F2=100 (Hz), with the bioelectrical impedance R being the same, a post-modification power consumption P2 is 9.6 (mW). From this it can be seen that the post-modification power consumption P2 is less than the pre-modification power consumption P1 and power consumption is reduced.

Figure 5:
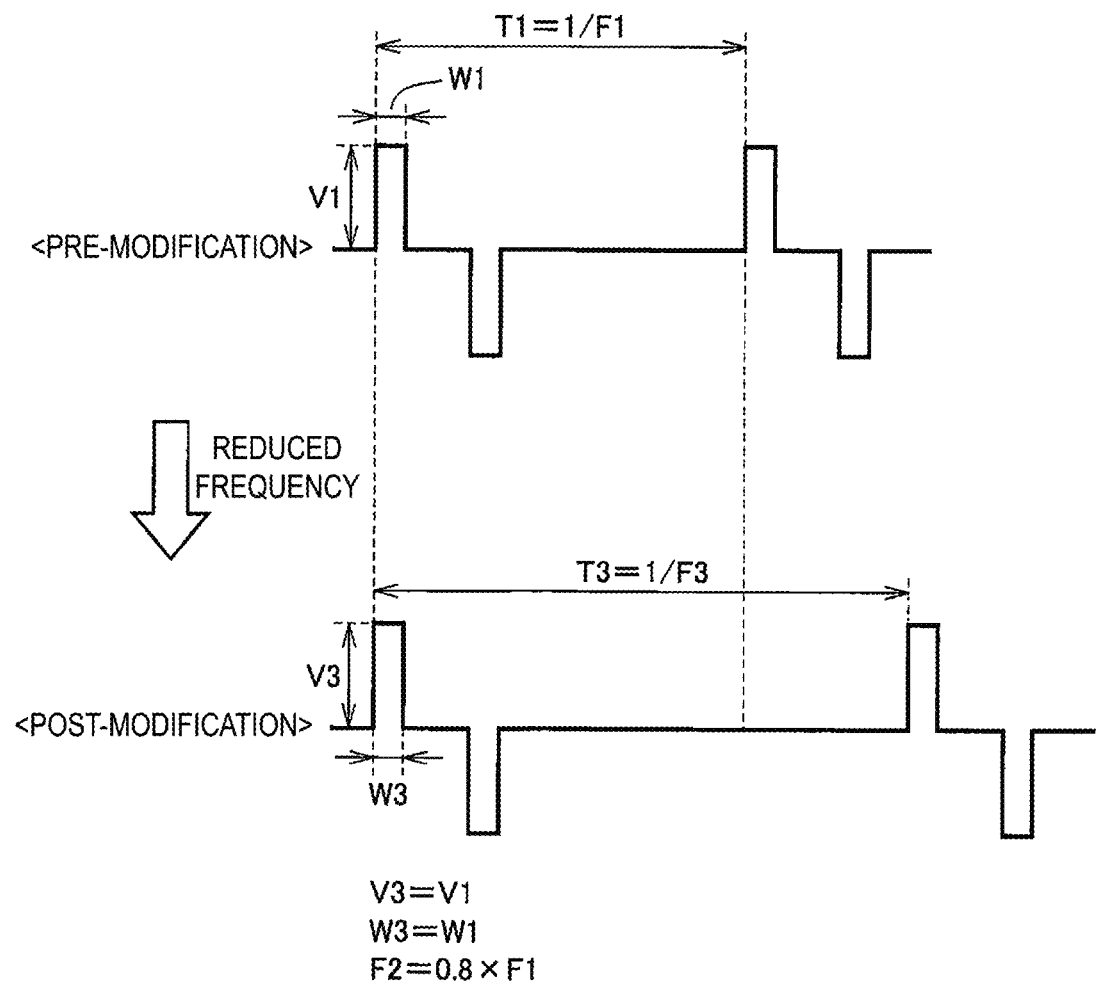
FIG. 5 is a diagram illustrating another example of a modified pattern of the pulse voltage waveform.

FIG. 5 is a diagram illustrating another example of a modified pattern of the pulse voltage waveform. Referring to FIG. 5, the parameters of the pre-modification pulse voltage waveform are the amplitude V1, the pulse width W1, and the pulse frequency F1. The parameters of the post-modification pulse voltage waveform are an amplitude V3 (=V1), a pulse width W3 (=W1), and a pulse frequency F3 (=0.8×F1). That is, compared to the pre-modification pulse voltage waveform, the post-modification pulse voltage waveform has a 20% reduced pulse frequency (the pulse period T is increased by 20%).

For example, substituting V1=50 (V), W1=50 (μs), F1=100 (Hz), and R=1 (kΩ) into Formula (1), a pre-modification power consumption P1 is 12.5 (mW). In this case, V3=50 (V), W3=50 (μs), and F3=80 (Hz), thus a post-modification power consumption P3 is 10 (mW). In the example of FIG. 5, it can be seen that power consumption is reduced.

In this manner, with the electrical treatment device 200 according to the first embodiment, the treatment time is guaranteed and the pulse voltage waveform is modified so that the change in the electrical stimulation provided to the user before and after modification is kept to a minimum (without simply decreasing the electrical stimulation intensity corresponding to the amplitude V).

Note that the above-described modified patterns are merely examples, and other modified patterns may be used. Also, the feeling of the electrical stimulation is different depending on the user. Thus, the electrical treatment device 200 may present to the user a plurality of modified patterns when it is determined that the treatment content cannot be fully executed on the basis of the current remaining battery power and the power consumption calculated from the pulse voltage waveform corresponding to the treatment content currently set. Specifically, the user experiences the electrical stimulations produced by various modified patterns and selects their preferred modified pattern. The pulse voltage waveform is modified in accordance with the modified pattern selected.

To describe in more detail, the electrical treatment device 200 outputs a pulse voltage waveform in accordance with a modified pattern K1 of FIG. 4 (i.e., a pattern with a decreased amplitude and an increased pulse width) for a predetermined amount of time (for example, ten seconds). Next, the electrical treatment device 200 outputs a pulse voltage waveform in accordance with a modified pattern K2 of FIG. 5 (i.e., a pattern with a decreased frequency) for a predetermined amount of time. Then, the electrical treatment device 200 displays a screen on the display 260 prompting for selection of one of the modified patterns. The electrical treatment device 200 receives input of a desired modified pattern (for example, the modified pattern K2) by the user via the operation interface 230 and modifies the pulse voltage waveform to a pulse voltage waveform that corresponds to the received modified pattern. This allows the user to receive their preferred treatment until the treatment time has elapsed.

Functional Configuration

Figure 6:
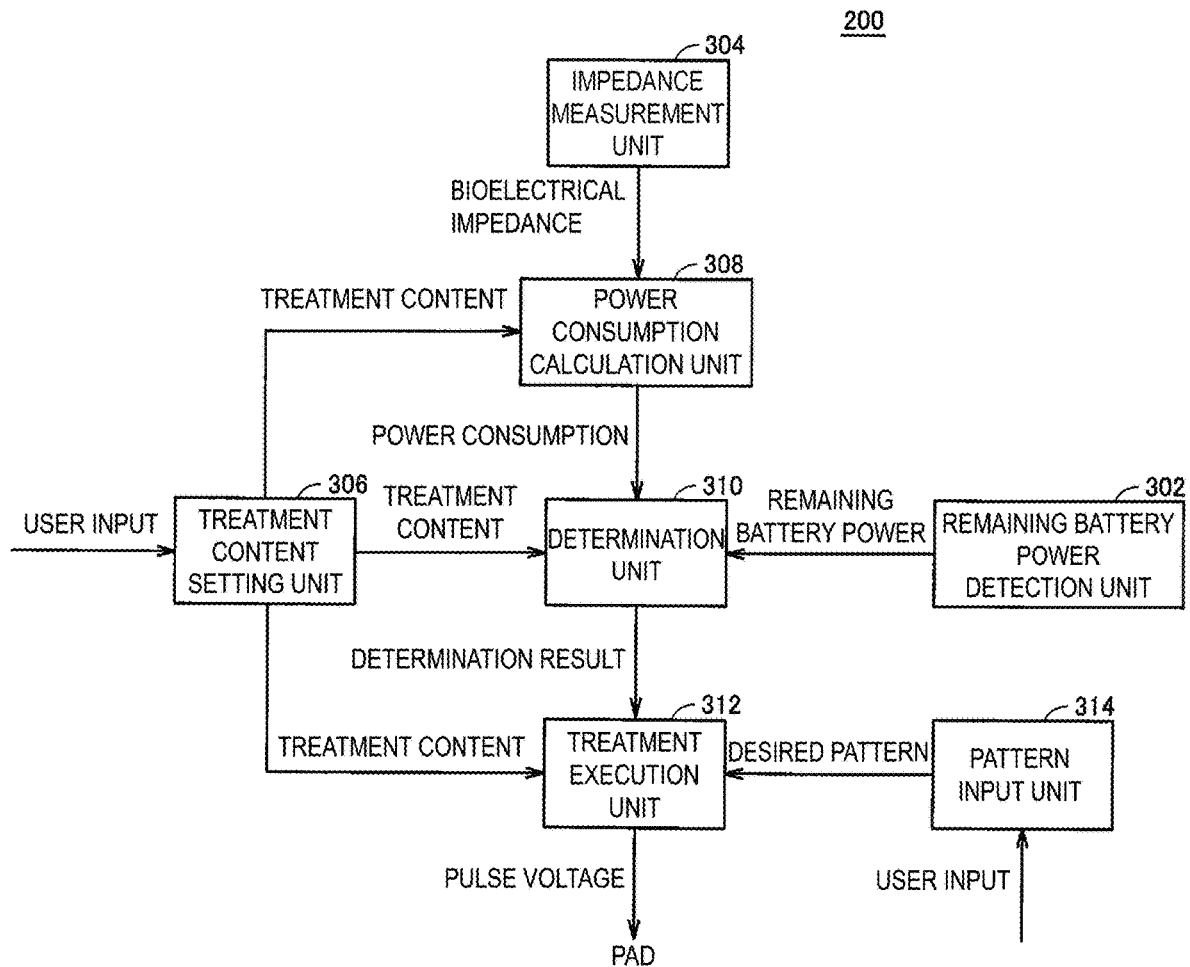
FIG. 6 is a block diagram illustrating a functional configuration of the electrical treatment device according to the first embodiment.

FIG. 6 is a block diagram illustrating a functional configuration of the electrical treatment device 200 according to the first embodiment. Referring to FIG. 6, the electrical treatment device 200 includes, as a main configuration, a remaining battery power detection unit 302, an impedance measurement unit 304, a treatment content setting unit 306, a power consumption calculation unit 308, a determination unit 310, a treatment execution unit 313, and a pattern input unit 314.

The remaining battery power detection unit 302 detects the remaining battery power of the electrical treatment device 200 (specifically, the battery 240). For example, the remaining battery power detection unit 302 measures the battery voltage (direct current voltage) of the battery 240 and detects the current remaining battery power on the basis of information indicating a corresponding relationship between the remaining battery power and the battery voltage. Typically, the remaining battery power detection unit 302 is realized by the processor 210.

The impedance measurement unit 304 measures the bioelectrical impedance R of the treatment site by using electrodes (electrodes of the pair of pads 270) that come into contact with the user's body at the treatment site. Specifically, when the pair of pads 270 is attached to the user, the impedance measurement unit 304 measures the bioelectrical impedance R of the treatment site on the basis of the value of the current flowing between the pair of pads 270 through the treatment site and the value of the voltage applied between the pair of pads 270.

In some embodiments, the impedance measurement unit 304 measures the bioelectrical impedance R after an instruction is provided from the user to start treatment and before the treatment of the treatment site is started by the treatment execution unit 313. Furthermore, in some embodiments, the impedance measurement unit 304 may measure the bioelectrical impedance R when an instruction is received from the user to start impedance measurement via the operation interface 230. Typically, the impedance measurement unit 304 is realized by the processor 210 and the waveform generation/output device 250.

The treatment content setting unit 306 sets the treatment content specified by the user. Specifically, the treatment content setting unit 306 receives a setting input of the treatment content via the operation interface 230. The treatment content includes the treatment mode and the electrical stimulation intensity. The treatment content setting unit 306 may accept from the user a setting input for the treatment time, which is the amount of time for performing the treatment in accordance with the treatment content. However, the treatment time may be a preset fixed amount of time. Typically, the treatment content setting unit 306 is realized by the processor 210.

The power consumption calculation unit 308 calculates the power consumption P on the basis of the bioelectrical impedance R and the parameters of the pulse voltage waveform corresponding to the treatment content. Specifically, the power consumption calculation unit 308 calculates the power consumption P by substituting the amplitude V, the pulse width W, the pulse frequency F, and the bioelectrical impedance R into Formula (1). Typically, the power consumption calculation unit 308 is realized by the processor 210.

The determination unit 310 determines whether treatment in accordance with the treatment content can be executed up until the treatment time elapses on the basis of the current remaining battery power and the power consumption P. Specifically, the determination unit 310 calculates the total power consumption Ph, which is the total energy used in the treatment time, from the treatment time and the power consumption P. Typically, when the current remaining battery power (remaining power of the battery) is greater than the total power consumption Ph by at least a predetermined value K, the determination unit 310 determines that treatment in accordance with the treatment content can be executed up until the treatment time elapses. When this is not true, the determination unit 310 determines that the treatment cannot be fully executed. Note that the predetermined value K is appropriately set taking into account a margin for the remaining battery power, the power used by the electrical treatment device 200 other than that included in the total power consumption Ph, and the like. Typically, the determination unit 310 is realized by the processor 210.

The treatment execution unit 313 performs treatment of the treatment site in accordance with the treatment content by controlling the voltage waveform applied to the electrodes. Typically, the treatment execution unit 313 is realized by the processor 210 and the waveform generation/output device 250.

In some embodiments, when the determination unit 310 determines that treatment in accordance with the treatment content cannot be executed up until the treatment time elapses, the treatment execution unit 313 modifies the pulse voltage waveform corresponding to the treatment content currently set so that the treatment can be executed up until the treatment time elapses and outputs the modified pulse voltage waveform.

Specifically, the treatment execution unit 313 modifies the pulse voltage waveform so that the current remaining battery power is greater than the total power consumption Ph calculated on the basis of the post-modification pulse voltage waveform by at least the predetermined value K.

Specifically, the treatment execution unit 313 modifies the pulse voltage waveform by reducing the amplitude of the pulse voltage waveform and increasing the pulse width (see FIG. 4). Alternatively, the treatment execution unit 313 modifies the pulse voltage waveform by reducing the frequency of the pulse voltage waveform (see FIG. 5).

In some embodiments, when treatment in accordance with the treatment content cannot be executed up until the treatment time elapses, the treatment execution unit 313 outputs pulse voltage waveforms corresponding to a plurality of modified patterns, each for a predetermined amount of time. The pattern input unit 314 receives an input of a modified pattern desired by the user from among a plurality of modified patterns via the operation interface 230. Typically, the pattern input unit 314 is realized by the processor 210. The treatment execution unit 313 modifies the pulse voltage waveform corresponding to the treatment content currently set to a pulse voltage waveform corresponding to the received modified pattern and outputs the modified pulse voltage waveform.

In addition, when the treatment content is changed by the user during treatment of the treatment site by the treatment execution unit 313 (for example, the treatment mode and/or the electrical stimulation intensity is changed), the treatment content setting unit 306 outputs the treatment content to the power consumption calculation unit 308, the determination unit 310, and the treatment execution unit 313.

The power consumption calculation unit 308 re-calculates the power consumption P on the basis of the bioelectrical impedance R and the parameters of the pulse voltage waveform corresponding to the changed treatment content. The determination unit 310 determines whether treatment in accordance with the changed treatment content can be executed up until the treatment time elapses on the basis of the current remaining battery power and the re-calculated power consumption P.

In the case where the treatment in accordance with the changed treatment content can be executed up until the treatment time elapses, the treatment execution unit 313 outputs a pulse voltage waveform corresponding to the changed treatment content. In the case where the treatment in accordance with the changed treatment content cannot be executed up until the treatment time elapses, the treatment execution unit 313 modifies the pulse voltage waveform corresponding to the changed treatment content so that the treatment can be executed up until the treatment time elapses and the modified pulse voltage waveform is output.

Processing Procedure

Figure 7:
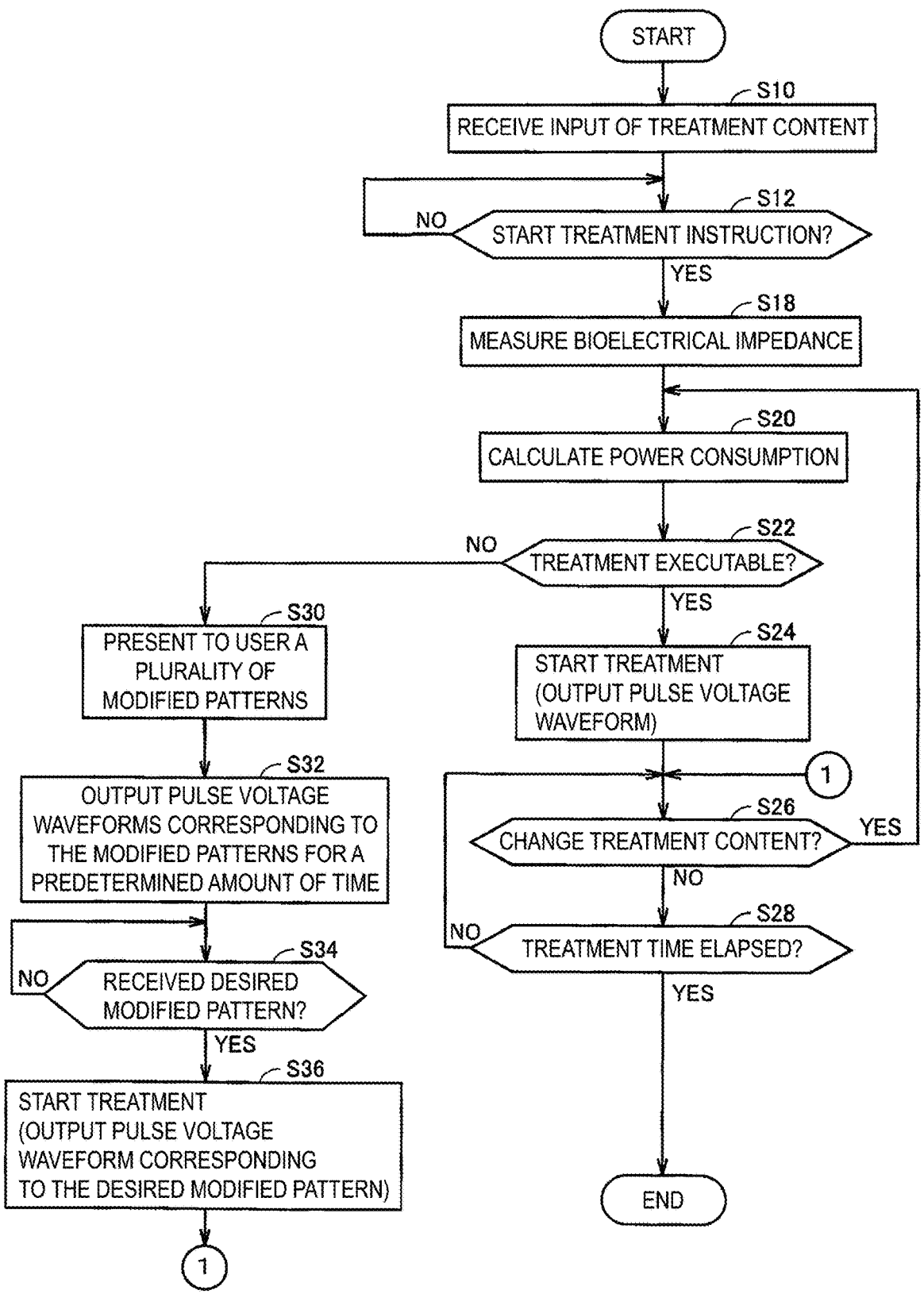
FIG. 7 is a flowchart illustrating an example of a processing procedure of the electrical treatment device according to the first embodiment.

FIG. 7 is a flowchart illustrating an example of a processing procedure of the electrical treatment device 200 according to the first embodiment. Each step in FIG. 7 is mainly performed by the processor 210 of the electrical treatment device 200. Note that, during the process described below, the electrical treatment device 200 constantly applies a minute voltage to the pair of pads 270 to determine whether the pair of pads 270 are properly installed. In the case where the pair of pads 270 are not properly installed, the electrical treatment device 200 displays on the display 260 information prompting for the pair of pads 270 to be attached to the treatment site.

Referring to FIG. 7, the electrical treatment device 200 receives a setting input of the treatment content via the operation interface 230 (step S10). Specifically, the electrical treatment device 200 receives a setting input for the treatment mode and the electrical stimulation intensity.

The electrical treatment device 200 determines whether a start treatment instruction has been received via the operation interface 230 (step S12). If the instruction has not been received (NO in step S12), then the electrical treatment device 200 repeats the process of step S12. If the instruction has been received (YES in step S12), the electrical treatment device 200 measures the bioelectrical impedance R by running a minute current to the treatment site through the pair of pads 270 (step S18).

The electrical treatment device 200 calculates the power consumption P on the basis of the measured bioelectrical impedance R and the parameters of the pulse voltage waveform corresponding to the treatment content set in step S10 (step S20). The electrical treatment device 200 determines whether treatment in accordance with the treatment content can be executed up until the treatment time elapses on the basis of the current remaining battery power and the total power consumption Ph calculated from the power consumption P and the treatment time (step S22).

If the treatment can be executed (YES in step S22), the electrical treatment device 200 starts treatment by outputting a pulse voltage waveform corresponding to the treatment content (step S24). Then, the electrical treatment device 200 determines whether a change settings input for changing the settings of the treatment content has been received from the user via the operation interface 230 (step S26). If the change settings input has been received (YES in step S26), the electrical treatment device 200 returns to step S20. That is, the electrical treatment device 200 re-calculates the power consumption P on the basis of the bioelectrical impedance R and the parameters of the pulse voltage waveform corresponding to the changed treatment content.

If the change settings input has not been received (NO in step S26), the electrical treatment device 200 determines whether the treatment time has elapsed (step S28). If the treatment time has not elapsed (NO in step S28), then the electrical treatment device 200 returns to step S26. That is, the electrical treatment device 200 continues treatment. If the treatment time has elapsed (YES in step S28), then the electrical treatment device 200 ends the process.

Returning now to step S22, if the electrical treatment device 200 determines that treatment in accordance with the treatment content cannot be executed up until the treatment time elapses (NO in step S22), the electrical treatment device 200 presents to the user a plurality of modified patterns relating to the pulsed voltage waveform (step S30). Specifically, the electrical treatment device 200 displays on the display 260 icons of the modified patterns and prompts for selection of the icons.

The electrical treatment device 200 outputs pulse voltage waveforms corresponding to the modified patterns for a predetermined amount of time (step S32). For example, when a selection input of the icon corresponding to the modified pattern K1 is received, the electrical treatment device 200 outputs a pulse voltage waveform corresponding to the modified pattern K1 for a predetermined amount of time. Similarly, the electrical treatment device 200 outputs a pulse voltage waveform corresponding to another modified pattern for a predetermined amount of time. This allows the user to determine which is their preferred treatment from among treatments corresponding to modified patterns.

The electrical treatment device 200 determines whether a selection input of the desired modified pattern has been received (step S34). If the selection input has not been received (NO in step S34), then the electrical treatment device 200 returns to step S34. If the selection input has been received (YES in step S34), the electrical treatment device 200 starts treatment by outputting a pulse voltage waveform corresponding to the desired modified pattern (step S36) and the process of step S26 is executed.

Advantages

According to the first embodiment, the pulse voltage waveform is modified to allow treatment to continue until completion on the basis of the current remaining battery power. This can prevent treatment from being interrupted due to running too low on remaining battery power. Also, the user can fully receive a pleasing treatment.

Second Embodiment

System Configuration

The first embodiment described above has a configuration in which the user is treated with a single electrical treatment device. In the second embodiment described below has a configuration in which a terminal device and an electrical treatment device are wirelessly connected and the electrical treatment device performs treatment in accordance with an instruction from the terminal apparatus. Note that the terminal device mainly serves as the operation interface 230 and the display 260 of the electrical treatment device 200 according to the first embodiment.

Figure 8:
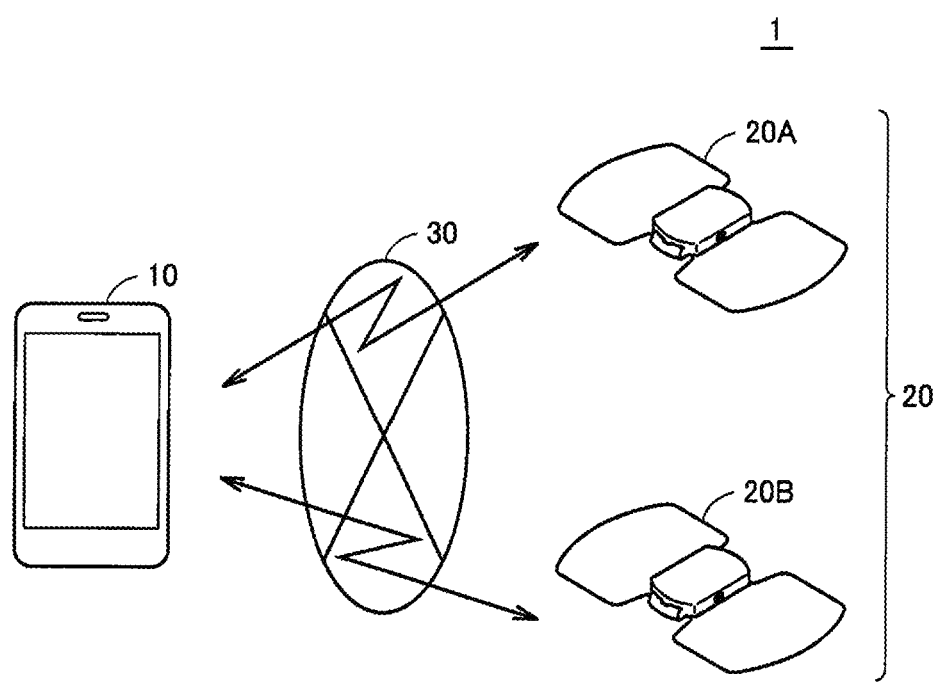
FIG. 8 is a diagram illustrating a schematic configuration of a treatment system according to a second embodiment.

FIG. 8 is a diagram illustrating a schematic configuration of a treatment system 1 according to the second embodiment. Referring to FIG. 8, the treatment system 1 includes a terminal device 10, which is a user terminal, electrical treatment devices 20A, 20B, and a network 30. Hereinafter, when describing configurations and functions shared by the electrical treatment devices 20A, 20B, the electrical treatment devices 20A, 20B are collectively referred to as an "electrical treatment device 20".

The electrical treatment device 20 is a cordless type and includes a pad, a holder, and a main body portion that serve as a single unit when used. These portions are used in combination to provide treatment. The specific configuration of the electrical treatment device 20 will be described later.

The terminal device 10 is, for example, a smart phone including a touch panel. In the description hereinafter, a smartphone will be used as a representative example of the "terminal device". However, the terminal device may be a different terminal device such as a folding type mobile telephone, a tablet terminal device, a personal computer (PC), and a personal data assistance (PDA).

The network 30 for connecting the terminal device 10 and the electrical treatment device 20 employs a short-range wireless communication system, typically Bluetooth (trademark) low energy (BLE). As such, the terminal device 10 and the electrical treatment device 20 are BLE devices having a function of performing wireless communication using BLE. However, the network 30 is not limited thereto, and a different wireless communication system, such as Bluetooth (trade name) or a wireless local area network (LAN), may be employed.

In the treatment system 1 according to the second embodiment, the terminal device 10 gives instructions to the electrical treatment devices 20A, 20B paired therewith via an application installed on the terminal device 10. The terminal device 10 displays various kinds of information on a display 158 of the terminal device 10 and notifies the user of necessary information. For example, the terminal device 10 may display information received from the electrical treatment device 20 on the display 158.

Configuration of Electrical Treatment Device 20

Figure 9:
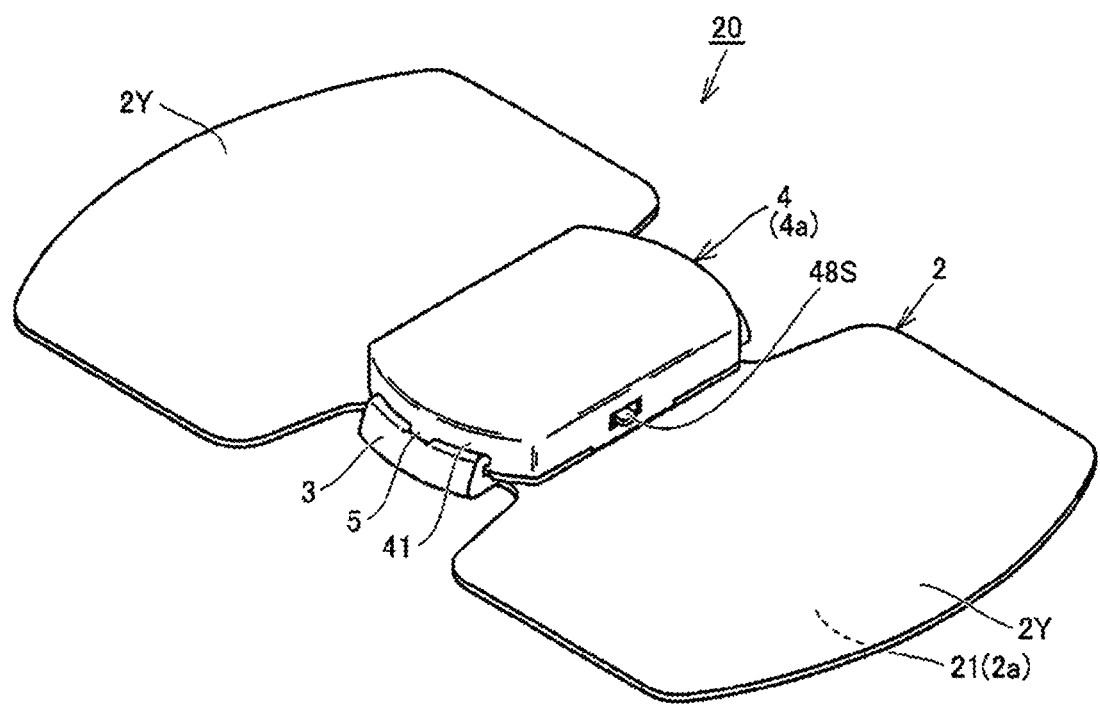
FIG. 9 is a perspective view illustrating a configuration of an electrical treatment device according to the second embodiment.
Figure 10:
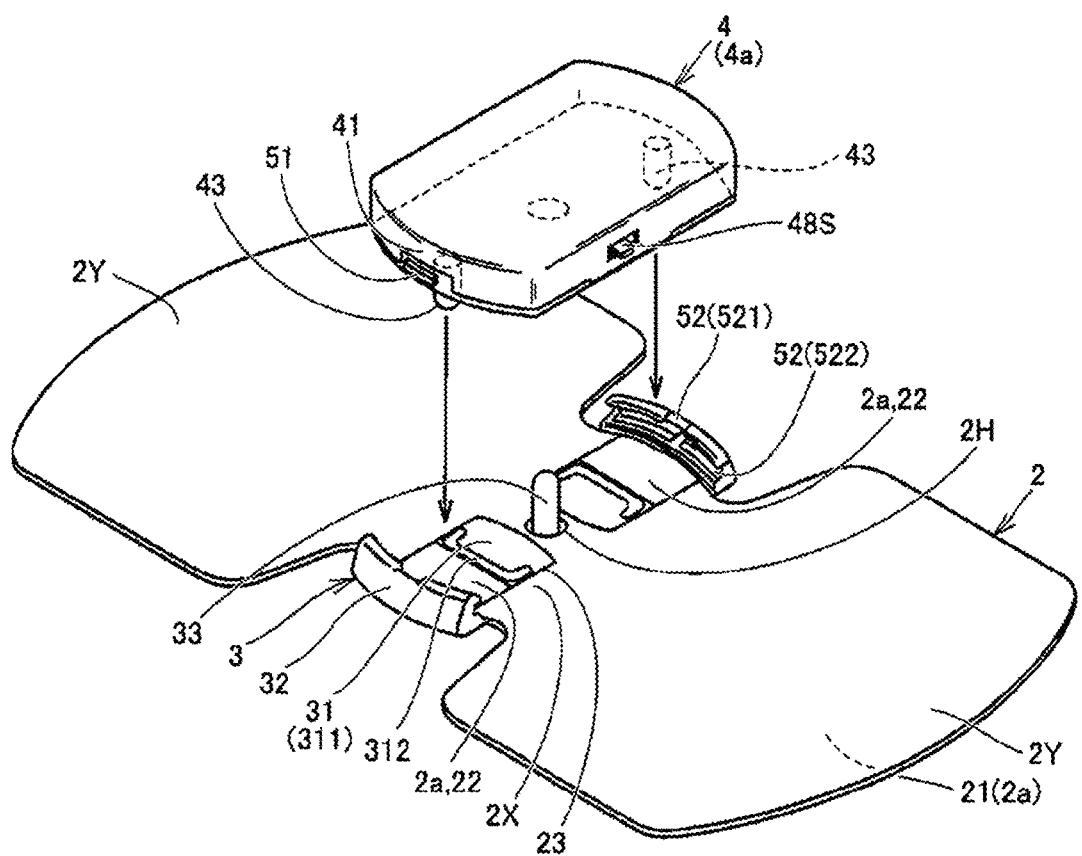
FIG. 10 is a perspective view illustrating a main body portion, a holder, and a pad of the electrical treatment device according to the second embodiment, in a state where the main body portion is separated from the holder and the pad.

FIG. 9 is a perspective view illustrating the configuration of the electrical treatment device 20 according to the second embodiment. FIG. 10 is a perspective view illustrating a main body portion 4, a holder 3, and a pad 2 of the electrical treatment device 20 according to the second embodiment, in a state where the main body portion 4 is separated from the holder 3 and the pad 2.

Referring to FIGS. 9 and 10, the electrical treatment device 20 is a so-called cordless type low-frequency treatment device and includes the pad 2, the holder 3, and the main body portion 4.

The pad 2 has a sheet-like shape and is configured to attach to the user's body. A conductive layer 2a is provided on a body-side portion 21 surface (lower surface), of the outer surfaces of the pad 2, that faces the body. The pad 2 is attached to the user's skin by using a conductive gel or the like, and a low-frequency pulse is supplied to the user through the conductive layer 2a.

Referring to FIG. 10, the pad 2 includes an attachment portion 2X and a treatment portion 2Y. The attachment portion 2X is held by the holder 3. A window portion 23 and a through hole 2H are provided at the attachment portion 2X. A positioning protrusion 312 of the holder 3 is disposed on the inside of the window portion 23. An interlock pin 33 of the holder 3 is inserted through the through hole 2H. The treatment portion 2Y is provided on both the left and right sides of the attachment portion 2X, and the conductive layer 2a is exposed on the body-side portion 21 of the treatment portion 2Y.

The conductive layer 2a is also exposed on the surface facing the main body portion 4 at the attachment portion 2X, and the exposed portion constitutes a pad side electrode portion 22. The pad side electrode portion 22 is formed to establish an electrical connection with a main body portion side electrode portion 43, and a conductive layer 2a corresponding to one electrode portion (for example, a positive electrode) is exposed at one end of the attachment portion 2X, and a conductive layer 2a corresponding to another electrode portion (for example, a negative electrode) is exposed at the other end of the attachment portion 2X.

Referring to FIG. 10, the holder 3 includes a pad holding portion 31 with a plate-like shape and a pair of wall portions 32 erected from both ends of the pad holding portion 31. An attachment portion 2X of the pad 2 is disposed on an upper surface 311 of the pad holding portion 31. Double-sided adhesive tape, glue, adhesive, or the like is disposed, as necessary, between the upper surface 311 and the attachment portion 2X.

The positioning protrusion 312 is provided on the pad holding portion 31. By fitting the inner peripheral edge of the window portion 23 provided in the pad 2 to the positioning protrusion 312, the pad 2 can be positioned with respect to the holder 3. The interlock pin 33 is centrally disposed on the pad holding portion 31. When attaching the pad 2 to the holder 3, the interlock pin 33 is inserted into the through hole 2H.

The pad 2 is a consumable item, and the pad 2 can be detachably attached to the main body portion 4, thus allowing replacement of the pad 2. In the present embodiment, the holder 3 holds the pad 2 such that the holder 3 and the pad 2 are integrated, and the main body portion 4 is configured to be detachably attached to the pad 2 and the holder 3. The pad 2 can be replaced together with the holder 3, or it is also possible to reuse the holder 3 as necessary.

Referring to FIGS. 9 and 10, the main body portion 4 includes as an outer cover a case 4a with a substantially rectangular parallelepiped shape. A guiding/engagement portion 5 (FIG. 9) is formed between the case 4a and the holder 3, and the main body portion 4 (case 4a) is detachably attached to the holder 3. The guiding/engagement portion 5 includes a protrusion 51 (FIG. 10) formed on a side surface 41 of the case 4a and a groove portion 52 (FIG. 10) formed in each of the wall portions 32 of the holder 3.

Referring to FIG. 10, the groove portion 52 includes a vertical groove portion 521 and a lateral groove portion 522. The vertical groove portion 521 is formed in the vertical direction and opens upward. The lateral groove portion 522 is formed in the lateral direction and opens at both ends. When the main body portion 4 is attached to the holder 3, both of the protrusion 51 and the groove portion 52 move closer together in a facing direction and engage together. By rotating and moving the main body portion 4 with respect to the holder 3, the engagement between the two is released, and the main body portion 4 can be removed from the holder 3.

With the main body portion 4 attached to the holder 3, the main body portion 4 supplies a low-frequency pulse current to the conductive layer 2a of the pad 2. Specifically, the main body portion 4 includes a pair of the main body portion side electrode portions 43, a substrate (not illustrated), an electric circuit (not illustrated), and an interlock mechanism (not illustrated). The electric circuit includes various control devices and is mounted on the surface of the substrate.

Examples of the control devices include a processor for performing various processes, a memory for storing programs, data, and the like, a communication interface for wirelessly communicating various types of data with the terminal device 10, and a waveform generation/output device for boosting the power source voltage and generating and outputting a low-frequency pulse current (treatment current).

The substrate, the electric circuit, and the interlock mechanism are provided inside the main body portion 4 (case 4a). A power source (not illustrated) such as a battery is also provided inside the main body portion 4 (case 4a). A switch 48S, a display portion (not illustrated) such as a light emitting diode (LED), and a button (not illustrated) are provided on the outside of the case 4a.

In a state in which the main body portion 4 is attached to the holder 3, an end portion of the main body portion side electrode portion 43 abuts the pad side electrode portion 22. Thus, the main body portion side electrode portion 43 and the pad side electrode portion 22 are electrically connected, whereby the electric circuit can supply a low-frequency pulse current to the pad side electrode portion 22.

Configuration of Terminal Device 10

Figure 11:
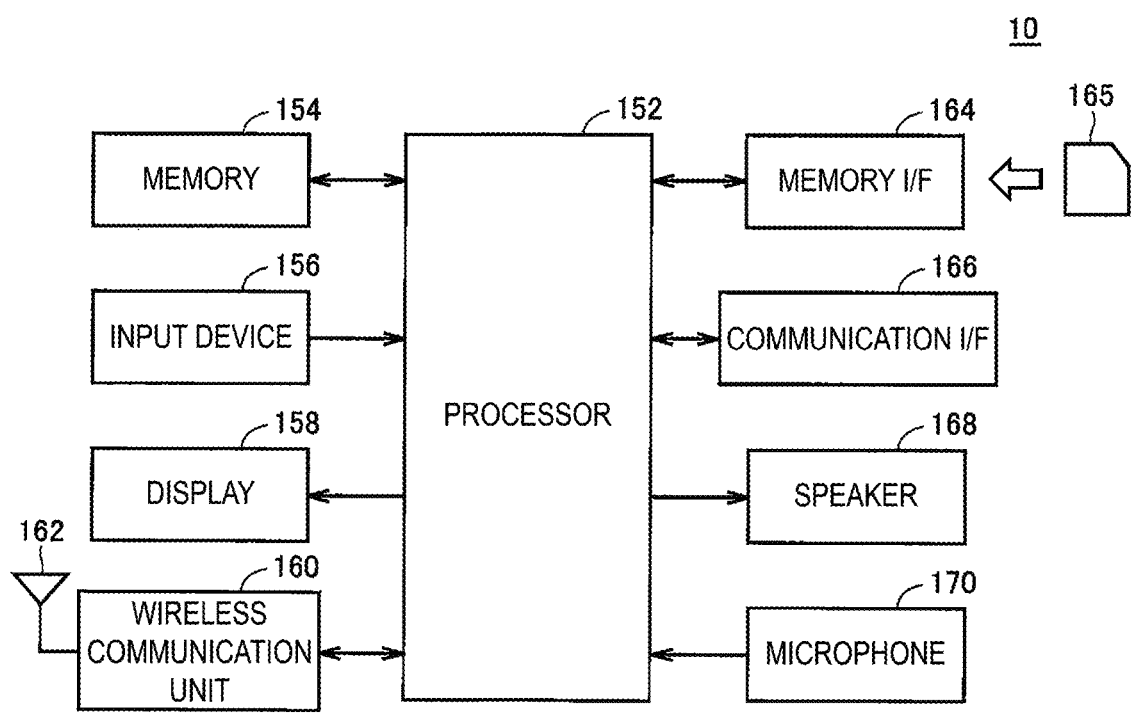
FIG. 11 is a block diagram illustrating an example of a hardware configuration of a terminal device according to the second embodiment.

FIG. 11 is a block diagram illustrating an example of a hardware configuration of the terminal device 10 according to the second embodiment. Referring to FIG. 11, the terminal device 10 includes, as main components, a processor 152, a memory 154, an input device 156, a display 158, a wireless communication unit 160, a memory interface (I/F) 164, a communication interface (I/F) 166, a speaker 168, and a microphone 170.

The processor 152 typically may be an arithmetic processing unit such as a central processing unit (CPU) or a multi processing unit (MPU). The memory 154 is realized by random access memory (RAM), read-only memory (ROM), flash memory, and the like.

The input device 156 receives an operation input to the terminal device 10. Typically, the input device 156 is realized by a touch panel. The touch panel is provided on the display 158 that functions as a display portion, and is, for example, an electrostatic capacitive type. The touch panel detects touch operations on the touch panel by an external object at predetermined intervals of time and inputs touch coordinates to the processor 152. However, the input device 156 may include a button or the like.

The wireless communication unit 160 connects to a mobile communication network via a communication antenna 162 and transmits and receives signals for wireless communication. Accordingly, the terminal device 10 can communicate with other communication devices via a mobile communication network such as Long Term Evolution (LTE), for example.

The memory interface 164 reads data from an external storage medium 165. The processor 152 reads the data stored in the storage medium 165 via the memory interface 164 and stores the data in the memory 154. The processor 152 reads the data from the memory 154 and stores the data in the external storage medium 165 via the memory interface 164.

The storage medium 165 may also be media that store programs in a non-volatile manner, such as a compact disc (CD), digital versatile disk (DVD), Blu-ray (trademark) disc (BD), universal serial bus (USB) memory, secure digital (SD) memory card.

The communication interface (I/F) 166 is a communication interface for exchanging various data between the terminal device 10 and the electrical treatment device 20 and is realized by an adapter, a connector, or the like. As the communication method, for example, a wireless communication method such as Bluetooth (trademark) low energy (BLE), and wireless LAN may be employed.

The speaker 168 converts an audio signal from the processor 152 to voice and outputs the same to the outside of the terminal device 10. The microphone 170 receives an audio input for the terminal device 10 and provides to the processor 152 an audio signal corresponding to the audio input.

Functional Configuration

The electrical treatment device 20 has a function similar to that of the electrical treatment device 200 described above. In particular, functions similar to those of the electrical treatment device 200 illustrated in FIG. 6 are realized by a control device included in the main body portion 4 of the electrical treatment device 20. In the first embodiment, the user provides instructions to the electrical treatment device 200 via the operation interface 230. In the second embodiment, the user provides instructions to the terminal device 10 via the input device 156, and the instructions are sent from the terminal device 10 to the electrical treatment device 20. In this way, various instructions are indirectly provided to the electrical treatment device 20.

Also, the first embodiment has a configuration in which the treatment current flows to the treatment site by a voltage being applied between the electrode of one of the pads 270 with a positive polarity and the electrode of the other pad 270 with a negative polarity. The second embodiment has a configuration in which two electrode portions, one having a positive polarity and the other having a negative polarity, are formed on one pad 2, and the treatment current flows to the treatment site by a pulse voltage waveform being applied between the electrodes.

Also, the various information is stored in the memory 220 used by the electrical treatment device 200 for various processes in the first embodiment. In the second embodiment, such information is typically stored in the memory of the electrical treatment device 20. However, in another embodiment, a portion of the information is stored in the memory 154 of the terminal device 10.

Note that the electrical treatment device 20 may have a configuration in which information necessary to notify the user about, information for storing in the terminal device 10, and the like is sent to the terminal device 10.

Other Embodiments (1) The first embodiment described above has a configuration using the pair of pads 270, but the configuration is not limited thereto. Some embodiments may have a configuration in which an electrode for positive polarity and an electrode for negative polarity are formed on a single pad.

(2) In the embodiments described above, a program may be provided that causes a computer to function and execute controls such as those described in the flowcharts described above. Such a program can also be provided as a program product stored on a non-temporary computer-readable recording medium attached to a computer, such as a flexible disk, a compact disk read only memory (CD), a secondary storage device, a main storage device, and a memory card. Alternatively, a program may be provided, which is stored on a recording medium such as a hard disk built into a computer. The program may also be provided by download via a network.

With the program, required modules from among program modules provided as part of the computer operating system (OS) may be called in a predetermined sequence at a predetermined timing to execute processing. In this case, the modules described above are not included in the program per se, and the process is executed in cooperation with the OS. Programs that do not include such modules may also be included in the program according to the present embodiment.

In addition, the program according to the present embodiment may be provided integrated into a part of a different program. In this case as well, the program according to the present embodiment per se does not include the modules included in the different program described above, and the process is executed in cooperation with the different program. Such a program integrated in a different program shall also be within the scope of the program according to the present embodiment.

(3) The configuration given as an example of the embodiment described above is an example configuration of the present invention. The configuration can be combined with other known technology, and parts thereof may be omitted or modified within the scope of the present invention. Furthermore, the processes and configurations of other embodiments may be employed as appropriate to the embodiments described above.

The embodiments described herein are illustrative in all respects and are not intended as limitations. The scope of the present invention is indicated not by the descriptions above but by the claims and includes all meaning equivalent to the scope and changes within the scope.

REFERENCE SIGNS LIST

1 Treatment system
2, 270 Pad
2H Through hole
2X Attachment portion
2Y Treatment portion
2a Conductive layer
3 Holder
4, 205 Main body portion
4a Case
5 Guiding/engagement portion
10 Terminal device 20, 20A, 20B, 200 Electrical treatment device
21 Body-side portion
22 Pad side electrode portion
23 Window portion
30 Network
31 Pad holding portion
32 Wall portion
33 Interlock pin
41 Side surface
43 Main body portion side electrode portion
48S Switch
51 Protrusion
52 Groove portion
152, 210 Processor
154, 220 Memory
156 Input device
158, 260 Display
160 Wireless communication unit
162 Communication antenna
164 Memory interface
165 Storage medium
168 Speaker
170 Microphone
230 Operation interface
232 Power button
234 Mode selection button
236 Treatment start button
238 Adjustment button
240 Battery
250 Waveform generation/output device
280 Cord
282 Plug
302 Remaining battery power detection unit
304 Impedance measurement unit
306 Treatment content setting unit
308 Power consumption calculation unit
310 Determination unit
311 Upper surface
312 Positioning protrusion
313 Treatment execution unit
314 Pattern input unit
521 Vertical groove portion
522 Lateral groove portion

The invention claimed is:

1. An electrical treatment device, comprising:
a remaining power detection unit configured to detect a remaining battery power of the electrical treatment device;
a treatment content setting unit configured to set a treatment content specified by a user;
an impedance measurement unit configured to measure a bioelectrical impedance of a site on a body of the user by using electrodes that come into contact with the site;
a treatment execution unit configured to perform treatment of the site in accordance with the treatment content by controlling a voltage waveform applied to the electrodes; and
a determination unit configured to determine whether treatment in accordance with the treatment content can be executed up until a treatment time elapses on the basis of a current remaining battery power and a power consumption calculated from the bioelectrical impedance and the voltage waveform; wherein
when treatment in accordance with the treatment content cannot be executed up until the treatment time elapses, the treatment execution unit is configured to output voltage waveforms corresponding to a plurality of patterns for a predetermined amount of time;
the electrical treatment device further comprises an input unit configured to receive an input of a desired pattern from the user, the desired pattern being one of the plurality of patterns; and
the treatment execution unit is configured to modify the voltage waveform corresponding to the treatment content currently set to a voltage waveform corresponding to the pattern received.

2. The electrical treatment device according to claim 1, wherein
the treatment execution unit is configured to modify the voltage waveform by reducing an amplitude of the voltage waveform and increasing a pulse width of the voltage waveform.

3. The electrical treatment device according to claim 1, wherein
the treatment execution unit is configured to modify the voltage waveform by reducing a frequency of the voltage waveform.

4. The electrical treatment device according to claim 1, wherein
the electrical treatment device is a low-frequency treatment device.

5. An electrical treatment device, comprising:
a remaining power detection unit configured to detect a remaining battery power of the electrical treatment device;
a treatment content setting unit configured to set a treatment content specified by a user;
an impedance measurement unit configured to measure a bioelectrical impedance of a site on a body of the user by using electrodes that come into contact with the site;
a treatment execution unit configured to perform treatment of the site in accordance with the treatment content by controlling a voltage waveform applied to the electrodes; and
a determination unit configured to determine whether treatment in accordance with the treatment content can be executed up until a treatment time elapses on the basis of a current remaining battery power and a power consumption calculated from the bioelectrical impedance and the voltage waveform; wherein
when treatment in accordance with the treatment content cannot be executed up until the treatment time elapses, the treatment execution unit is configured to modify a voltage waveform corresponding to the treatment content currently set so that treatment can be executed up until the treatment time elapses, and outputs the modified voltage waveform, and
when the treatment content is changed by the user during treatment of the site by the treatment execution unit, the determination unit is configured to further determine whether treatment in accordance with a post-modification treatment content can be executed up until the treatment time elapses; and
in a case where treatment in accordance with the post-modification treatment content can be executed up until the treatment time elapses, the treatment execution unit is configured to output a voltage waveform corresponding to the post-modification treatment content.

6. The electrical treatment device according to claim 5, wherein the treatment execution unit is configured to modify the voltage waveform by reducing an amplitude of the voltage waveform and increasing a pulse width of the voltage waveform.

7. The electrical treatment device according to claim 5, wherein
the treatment execution unit is configured to modify the voltage waveform by reducing a frequency of the voltage waveform.

8. The electrical treatment device according to claim 5, wherein
the electrical treatment device is a low-frequency treatment device.

9. A control method of an electrical treatment device, comprising:
detecting a remaining battery power of the electrical treatment device;
setting a treatment content specified by a user;
measuring a bioelectrical impedance of a site on a body of the user by using electrodes that come into contact with the site;
executing treatment of the site in accordance with the treatment content by controlling a voltage waveform applied to the electrodes; and
determining whether treatment in accordance with the treatment content can be executed up until a treatment time elapses on the basis of a current remaining battery power and a power consumption calculated from the bioelectrical impedance and the voltage waveform; wherein
when treatment in accordance with the treatment content cannot be executed up until the treatment time elapses, wherein the executing includes outputting voltage waveforms corresponding to a plurality of patterns for a predetermined amount of time,
the control method comprising receiving an input of a desired pattern from the user, the desired pattern being one of the plurality of patterns, and
wherein the executing includes modifying the voltage waveform corresponding to the treatment content currently set to a voltage waveform corresponding to the pattern received.

10. A treatment system, comprising:
a terminal device; and
an electrical treatment device configured to wirelessly communicate with the terminal device; wherein
the electrical treatment device comprises
a remaining power detection unit configured to detect a remaining battery power of the electrical treatment device,
a treatment content setting unit configured to set a treatment content specified by a user,
an impedance measurement unit configured to measure a bioelectrical impedance of a site on a body of the user by using electrodes that come into contact with the site,
a treatment execution unit configured to perform treatment of the site in accordance with the treatment content by controlling a voltage waveform applied to the electrodes, and
a determination unit configured to determine whether treatment in accordance with the treatment content can be executed up until a treatment time elapses on the basis of a current remaining battery power and a power consumption calculated from the bioelectrical impedance and the voltage waveform; and
when treatment in accordance with the treatment content cannot be executed up until the treatment time elapses, the treatment execution unit is configured to voltage corresponding to output voltage waveforms corresponding to a plurality of patterns for a predetermined amount of time;
the electrical treatment device further comprises an input unit configured to receive an input of a desired pattern from the user, the desired pattern being one of the plurality of patterns; and
the treatment execution unit is configured to modify the voltage waveform corresponding to the treatment content currently set to a voltage waveform corresponding to the pattern received.

* * * * *